United States Patent [19]

Lococo

[11] Patent Number: 4,892,482
[45] Date of Patent: Jan. 9, 1990

[54] DENTAL RETRACTION CORD

[76] Inventor: Michael P. Lococo, 4999 Victoria Avenue, Niagara Falls, Ontario, Canada, L2E 4C9

[21] Appl. No.: 238,191

[22] Filed: Aug. 30, 1988

[51] Int. Cl.⁴ ............................................. A61C 5/14
[52] U.S. Cl. .................................................... 433/136
[58] Field of Search ....................... 433/136, 138, 139; 132/325

[56] References Cited

U.S. PATENT DOCUMENTS

| | | | |
|---|---|---|---|
| 2,174,796 | 10/1939 | Luzzi | 433/136 |
| 2,522,794 | 9/1950 | Medof | 132/325 |
| 4,321,038 | 3/1982 | Porteous | 433/136 |

FOREIGN PATENT DOCUMENTS

| | | | |
|---|---|---|---|
| 2919613 | 6/1980 | Fed. Rep. of Germany | 433/136 |
| 733649 | 7/1955 | United Kingdom | 433/136 |

Primary Examiner—John J. Wilson
Attorney, Agent, or Firm—Stevens, Davis, Miller & Mosher

[57] ABSTRACT

A gingival tissue retraction cord made, in the disclosed embodiment, of strands impregnated with suitable therapeutic preparations is stiffened with a stiffener strand, in the described example a copper wire threaded through the core of the cord. The stiffener is made of material which provides the cord with deformability, i.e. a feature whereby the cord can be bent but retains the bent or deformed state.

11 Claims, 1 Drawing Sheet

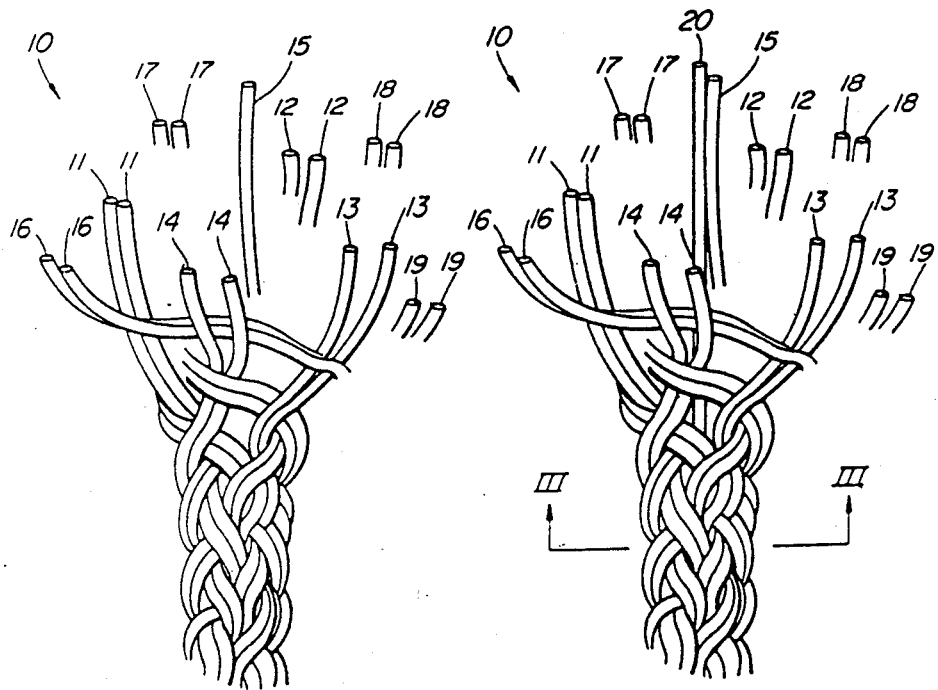
PRIOR ART
FIG. 1
FIG. 2
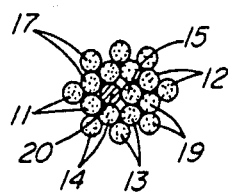
FIG. 3

DENTAL RETRACTION CORD

BACKGROUND OF THE INVENTION

The present invention relates to the art of dental retraction cords, also referred to as gingival retraction cords.

Present practice in crown and bridge work technique makes use of cords such as the braided gingival retraction cord described in U.S. Pat. No. 4,321,038, issued Mar. 23, 1982 to Don D. Porteous. The cord or string, which is usually impregnated with a vaso-constrictor, is unwound from a spool or withdrawn from a container. The dental practitioner estimates the length required and snips the desired length from the spool. He then wraps the cord around the tooth and either ties a knot to hold the cord in position on the cervical portion of the tooth, or overlays several turns of the cord on the tooth to hold the cord in place.

The practitioner then tucks the cord between the tooth and the gum tissue, to retract the gum tissue to thus enable an accurate taking of an accurate impression of the tooth inclusive of its cervical portion. Some retraction cords are made of strands impregnated with vaso-constrictors such as Epinephrine, or aluminum potassium sulfate. To this end it is desirable to produce the retraction cords from materials which are liquid permeable to facilitate impregnation thereof with suitable medicaments. One of the most recent developments in the structure of a dental retraction cord is shown in the above U.S. Patent to Porteous. It includes, apart from the braided absorbent strands, one or more strands disposed at the core of the cord and being adapted to prevent the flattening of the cord when disposed in the gingival sulcus. The invention described in the above patent somewhat increases the convenience of application of the retraction cord. Yet, the cord is still relatively difficult to pack into the gingival sulcus due to its inherent pliability which is due to the need for selecting strands of absorbent material, usually cotton.

SUMMARY OF THE INVENTION

It is an object of the present invention to further facilitate the application of the dental retraction cord.

In general terms, the present invention provides a dental retracting cord comprising a first longitudinal portion made of a liquid permeable material, and a second longitudinal stiffener portion generally integral with the first portion and being made of a generally non-resiliently deformable material having a form retaining capability greater than that of said first portion strands, to render the overall cord generally non-resiliently bendable in order to facilitate the application thereof.

The term "cord" within the context of the present invention is to be interpreted broadly and includes structures other than a braided cord. For instance, an elongated structure made of a felt-like material and provided with a stiffener member as set forth above is also intended to be included within the term of "cord".

In accordance with a preferred embodiment of the invention, a dental retraction cord is provided which comprises a plurality of flexible braided strands made of a liquid permeable material, and at least one stiffener strand generally integral with the cord and being made of a generally non-resiliently deformable material having a form retaining capability greater than that of said braided strands, to render the overall cord generally non-resiliently bendable in order to facilitate the application thereof.

According to another feature of the invention, the shape stiffener strand is a wire of malleable metallic material whose volume presents less than 1/6 of the overall volume of the cord as measured in a non-compressed, pre-application state of the cord. Preferably, the stiffener strand is a copper wire having the thickness of from about 0.2 millimeters to about 0.3 millimeters. It may be either braided into the cord, or can be simply threaded through the core thereof.

I have experimented with different kinds of wires, including gold wires but have discovered that there was little difference between an ordinary wire taken from a household electric cord and a gold wire of similar size.

The invention will now be described by way of a preferred embodiment, with reference to the accompanying drawings which show, in a diagrammatic fashion, a modification effected with one of the embodiments of the retraction cord described in the aforesaid U.S. Patent.

BRIEF DESCRIPTION OF THE DRAWINGS

In the drawings:

FIG. 1 is a perspective view of a dental retraction cord embodiment as shown in U.S. Pat. 4,321,038, the cord being a modified version;

FIG. 2 is a perspective view similar to that of FIG. 1 but showing the modification of the cord according to the present invention; and FIG. 3 is section III—III of FIG. 2, the view being on enlarged scale.

DETAILED DESCRIPTION

Turning firstly to the prior art representation in FIG. 1, reference numeral 10 generally denotes a braided gingival retraction cord. It has four pairs of warp strands 11, 12, 13 and 14, one axial support strand 15. The cord 10 further includes four pair of filling strands 16, 17, 18 and 19. As is well known in the art, each pair of the filling strands, e.g. filling strands 16, successively passes over and then under adjacent pairs of warp strands 13, 14 and each pair of warp strands, e.g. warp strands 14, successively passes over and then under adjacent pairs of filling strands 17, 16.

As described in the above U.S. Pat. No. 4,321,038, No. 60/2 cotton thread was employed for all strands, the braided retraction cord having fifty-two picks or plaits per linear inch and a diameter of about 0.5 mm (0.02 in.).

Using a regular sewing needle, I hand threaded through the centre or core of the above cord a copper wire taken from a household electric extension cord. The diameter of the wire was about 0.2 mm (about 0.015 in.). The wire, of course, was properly sterilized prior to its threading through the cord and the threading itself was carried out under sterile conditions, which included the sterilization of the needle used in threading the wire through the cord.

The final product is shown in FIGS. 2 & 3, wherein the corresponding parts of the Prior Art cord of FIG. 1 are shown with corresponding reference numerals. Thus, the only change in reference numerals of the drawings is in the wire being designated with reference numeral 20 and the overall modified cord being designated with reference numeral 21.

The modified retraction cord still had excellent pliability and was easy to bend and flex during the application. The substantial difference over the known cords was in that the packing was much easier as the cord retained the deformations imparted to it by the packing tool, which was entirely contrary to the behaviour of the Prior Art cord which was springy and thus much more difficult to Pack between the gingival tissue and the neck of the tooth.

An experiment wherein attempts were made to simulate the shape of the braided strands in the wire were less satisfactory even though the modified cord still had an improved shape-retaining capability over the Prior Art cord devoid of any stiffener wire.

It is obvious from the above that the stiffener strand or wire provides a substantial improvement over the existing dental retraction cords. The choice of the material suitable for the purpose is easy and those skilled in the art will readily appreciate that a large number of materials exists which are suitable for the stiffener strand described above. Malleable metal wires such as described above, i.e. a copper or gold containing alloy are readily available in the desired thickness and thus can be used without retarding the beneficial effect of the impregnation of the remaining strands of the cord with suitable therapeutic preparations. The interpretation of the term "cord" within the context of this specification and in particular the appended claims, is to be broad, as mentioned at the outset of the invention.

Accordingly, the above described embodiment is to be considered as strictly exemplary and not limiting the scope of protection afforded by a patent which may issue hereon. I wish to protect by such patent the scope commensurate with my contribution to the art.

I claim:

1. Dental retracting cord comprising a plurality of flexible braided strands made of a liquid permeable material, and at least one stiffener strand generally integral with the cord and continuously extending throughout the entire length thereof, said stiffener strand being made of a generally non-resiliently deformable material having a form retaining capability greater than that of said braided strands, to render the entire length of the cord generally non-resiliently bendable in order to facilitate the application thereof.

2. Dental retraction cord as claimed in claim 1, wherein said stiffener strand is a wire of malleable metallic material whose volume presents less than 1/6 of the overall volume of the cord as measured in a non-compressed, pre-application state of the cord.

3. Dental retraction cord as claimed in claim 2, wherein the stiffener strand is a copper wire having the thickness of from about 0.2 millimeters to about 0.3 millimeters.

4. Dental retraction cord as claimed in claims 1, wherein the stiffener strand is braided among the flexible braided strands.

5. Dental retraction cord as claimed in claims 1, wherein the stiffener strand extends along the axis of the cord.

6. Dental retraction cord as claimed in claims 1, wherein the stiffener strand is threaded longitudinally through the cord, whereby the stiffener strand generally co-incident with the axis of the cord.

7. Dental retracting cord having a predetermined length and comprising a first longitudinal portion made of a liquid permeable material, and a second longitudinal stiffener portion generally integral with the first portion, extending from one end of the first longitudinal portion to the other end thereof and being made of a generally non-resiliently deformable material having a form retaining capability greater than that of said first portion, to render the entire length of the cord generally non-resiliently bendable at any point of its length in order to facilitate the application thereof to retract gingival tissue from a cervical portion of a tooth.

8. Dental retraction cord as claimed in claim 7, wherein said stiffener portion is a wire of malleable metallic material whose volume presents less than 1/6 of the overall volume of the cord as measured in a non-compressed, pre-application state of the cord.

9. Dental retraction as claimed in claim 8, wherein the stiffener portion is a copper wire having the thickness of from about 0.2 millimeters to about 0.3 millimeters.

10. Dental retraction cord as claimed in claim 7, wherein the stiffener portion extends along the axis of the cord, on the surface of the first portion.

11. Dental retraction cord as claimed in claim 7, wherein the stiffener portion extends along the axis of the cord and is threaded in the first portion.

* * * * *